United States Patent [19]
Karady et al.

[11] 4,031,086
[45] June 21, 1977

[54] PROCESS FOR CLEAVAGE OF 7-AMINO-ADIPOYLAMINO SIDE CHAIN IN CEPHALOSPORINS
[75] Inventors: Sandor Karady, Mountainside, N.J.; Joseph S. Amato, Brooklyn, N.Y.
[73] Assignee: Merck & Co., Inc., Rahway, N.J.
[22] Filed: Mar. 5, 1976
[21] Appl. No.: 664,341
[52] U.S. Cl. ............................ 260/243 C; 424/246
[51] Int. Cl.² ...................................... C07D 501/04
[58] Field of Search ............................... 260/243 C
[56] References Cited
UNITED STATES PATENTS
3,957,771  5/1976  Bormann et al. .............. 260/243 C Primary Examiner—Nicholas S. Rizzo
Attorney, Agent, or Firm—Hesna J. Pfeiffer; Julian S. Levitt

[57] ABSTRACT

A process is provided for preparing an ester of 7-amino-7-methoxy-3-acetoxymethyl or methyl-2- or 3-cephem-4-carboxylic acid by reaction of an imino halide

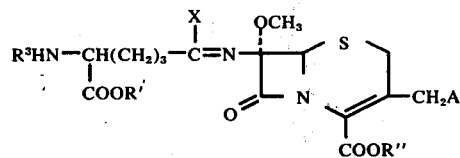

wherein R'' is a carboxyl blocking group, and $R^3$ is an amino protecting group, X is halo, preferably bromo or chloro, and A is hydrogen or acetoxy with the following cuprous methyl complex:

Li[MeCuBuO]

followed by reaction with aqueous ammonia to obtain the desired product.

4 Claims, No Drawings

PROCESS FOR CLEAVAGE OF 7-AMINO-ADIPOYLAMINO SIDE CHAIN IN CEPHALOSPORINS

SUMMARY OF THE INVENTION

The present invention provides a new method for preparing the cephalosporin nucleus compounds:

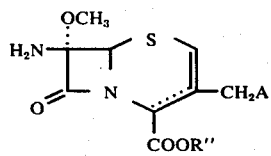
2 the dotted line represents that the unsaturation can be in the 2 or 3-position; and R″ is R′ or hydrogen, and R′ is a carboxylic protecting group which is alkyl of $C_1$–$C_6$, 2,2,2-trichlorethyl, 2-iodoethyl, tert-alkenyl or $C_5$–$C_7$, tert-alkynyl of $C_5$–$C_7$, benzyl, benzhydryl, nitrobenzyl, tetrahydropyranyl, succinimidomethyl, phthalimidomethyl, methoxybenzyl, dimethoxybenzyl, cyanomethyl, nitrophenyl, dinitrophenyl, 2,4,6-trinitrophenyl, bis(p-methoxyphenyl)-methyl, triphenylmethyl, diphenylmethyl, benzyloxymethyl, loweralkanoyloxymethyl of $C_3$–$C_6$, phenacyl, loweralkanoyl of $C_2$–$C_4$, or radical of the formula

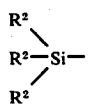

wherein each $R^2$ independently represents loweralkyl of $C_1$–$C_4$ or halo selected from the group consisting of bromo, chloro, fluoro, and iodo, subject to the limitation that at least one $R^2$ represents loweralkyl as defined. Preferred R″ blocking groups include methyl, benzyl, or benzhydryl.

The compounds are obtained by cleavage of the "α-amino-adipoyl" (5-amino-5-carboxyvaleryl) group from 7-(5-amino-5-carboxyvaleramido)-7-methoxycephalosporanic acid:

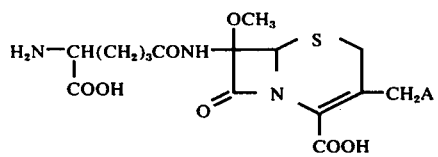
3 the compound wherein A is acetoxy is produced by fermentation of an organism identified as *Streptomyces lipmanii* NRRL 3584; the compound wherein A is hydrogen is produced by enzymatic deacetoxylation of the fermentation product.

The starting materials above must have the carboxylic acid and the amino groups protected before the process of this invention is employed. These protected starting materials are

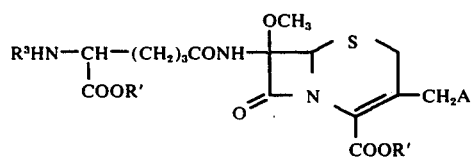
4 wherein R″ is as defined above, and $R^3$ is
alkanoyl of $C_1$–$C_4$,
aroyl of $C_7$–$C_{11}$,
alkoxycarbonyl of $C_2$–$C_5$,
benzyloxycarbonyl,
cycloalkoxycarbonyl of $C_6$–$C_7$,
aryloxycarbonyl of $C_7$–$C_{11}$,
one of the above groups substituted with from one to three groups, each selected from the group consisting of halo, nitro, loweralkoxy of $C_1$–$C_4$, cyano, and, in the instance of aroyl and aryloxy, loweralkyl of $C_1$–$C_4$, or phthaloyl, tosyl, or mesyl. "Halo" is employed to refer to bromo, chloro, iodo, and fluoro. Representative suitable groups include the following: mesyl, formyl, acetyl, propionyl, chloroacetyl, dichloroacetyl, benzoyl, p-nitrobenzoyl, phthaloyl, p-methoxybenzoyl, cyclohexyloxycarbonyl, tert-butoxycarbonyl, phenoxycarbonyl, benzyloxycarbonyl, and the like.

The blocked compounds of Formula 4 above are first treated with phosphorus pentachloride, phosgene, or a similar acid halide to form an imino halide, as described in Formula 1 above. While phosphorus pentachloride or phosgene are the preferred agents, other acid halides can be used. Thus, other suitable agents include phosphorus oxychloride, phosphorus trichloride, thionyl chloride, oxalyl chloride, and the complex compound formed from o-dihydroxybenzene and phosphorus trichloride.

The starting compound and the imino-halide-forming agent are reacted with one another in any convenient fashion. Generally the reaction consumes the reactants in amounts representing one molecular proportion of the starting compound and two molecular proportions of the imino-halide-forming agent. The reaction goes forward under temperatures of from −20° C to +50° C., but is preferably conducted at about ambient or room temperature. The reaction is preferably conducted in the presence of a tertiary amine, for example, triethylamine, pyridine, or dimethylaniline.

The resulting imino halide (1) is then reacted with the cuprous methyl complex

Li[MeCuBuO]

wherein Me is methyl, and BuO represents the t-butoxyl radical.

Approximately equimolar amounts are employed. The reaction is conducted at temperatures of about −100° C to 0° C, preferably about −25° to −10° C. The reaction mixture is then quenched by adding to a buffered salt solution of pH 7–8, and work-up in conventional fashion. The product is identified by NMR anaylsis.

The product prepared is that of Formula 2 above. Generally, the $\Delta^3$ isomer is isolated, but it is partially with the $\Delta^2$ form. The $\Delta^2$ isomer of the nucleus can be isomerized to the $\Delta^3$ compound using published methods which can then be acylated to $\Delta^3$-acylamino derivatives having antibacterial activity.

This invention is further illustrated by the following Example.

EXAMPLE 1

To a solution of 1.2 g. of 7-(5-phthalimido-5-carboxyvaleramido)-7-methoxy-3-methyl-3-cephem-4-carboxylic acid, dimethyl ester in 20 ml. of dry methylene chloride under nitrogen was added 5 ml. of dry pyridine followed by 20 ml. 1.2M phosgene in benzene. The mixture was kept at room temperature under nitrogen for 2 hours, then concentrated in vacuo, dissolved in tetrahydrofuran, and filtered to remove pyridine hydrochloride. The tetrahydrofuran solution was 20 ml. in volume.

The reagent [tBuOCH$_3$Cu$^-$]Li$^+$ was prepared by taking a solution of 1.5 mm. t-butanol in tetrahydrofuran at $-70°$ C., adding 0.9 ml. (1.7 m) methyllithium, warming to 0° C., then adding 360 mg. of cuprous chloride (Cu$_2$Cl$_2$). The solution was stirred at 0° C., and it was then an orange color. It was then cooled to $-70°$ C., and 0.9 ml. of methyllithium solution added, following which it was warmed to 0° C.

The solution of imidoylchloride of Step 1 and that of the cuprous complex were mixed at $-70°$ C., and the temperature raised to about 15° C. for 40 min. The reaction was then quenched by adding to a mixture of NaHCO$_3$, NH$_4$Cl at a pH = 7, extracted with ethyl acetate, and dried over MgSO$_4$. Work up with thin-layer chromatography yielded about 100 mg. of a compound identified as methyl 7-amino-7-methoxy-3-methyl-3-cephem-4-carboxylate using NMR analysis.

When this example is repeated using the 3-acetoxymethyl analogue, the corresponding analogue is isolated.

What is claimed is:

1. The process of preparing the compound of the formula:

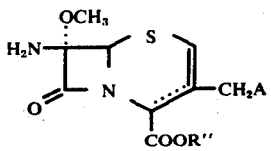

wherein the dotted line represents that the unsaturation can be in the 2- or the 3-position, A is hydrogen or acetoxy, and R" is methyl, benzyl or benzhydryl; which comprises reacting the compound

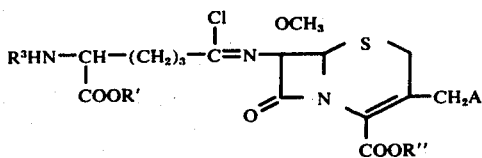

wherein R$^3$ is phthaloyl or mesyl, and R' and A are as defined;
in approximately equimolar amount with Li[MeCuBuO]

at a temperature between about $-100°$ C. to about 0° C.; followed by quenching in pH 7–8 buffer solution and recovering the desired product.

2. The process of claim 1 in which A is hydrogen.
3. The process of claim 1 in which R" is methyl.
4. The process of claim 1 in which R$^3$ is phthaloyl.

* * * * *

UNITED STATES PATENT AND TRADEMARK OFFICE
CERTIFICATE OF CORRECTION

PATENT NO. : 4,031,086
DATED : June 21, 1977
INVENTOR(S) : SANDOR KARADY et al.

It is certified that error appears in the above-identified patent and that said Letters Patent are hereby corrected as shown below:

At Col. 4, line 15, of Claim 1, cancel that structure and insert therefor --

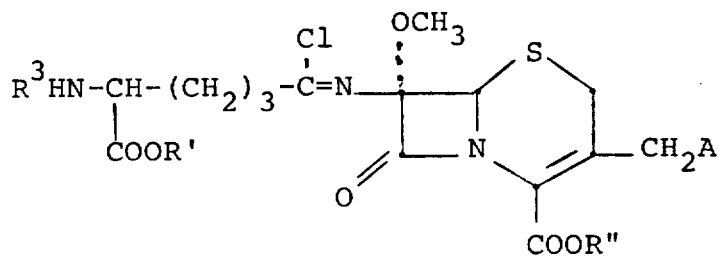

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*